(12) United States Patent
Caprio et al.

(10) Patent No.: US 9,024,619 B2
(45) Date of Patent: May 5, 2015

(54) CONNECTION SYSTEM FOR SENSOR DEVICE

(75) Inventors: Matthew Caprio, Seattle, WA (US);
Vanessa Beasley, Clayton, NC (US);
Gerald J. McMorrow, Redmond, WA (US); Andrew Clay, Everett, WA (US);
Ekaterina Filipova Ivanova, Kirkland, WA (US); Antonio Valenzuela, Everett, WA (US)

(73) Assignee: Verathon Inc., Bothell, WA (US)

( * ) Notice: Subject to any disclaimer, the term of this patent is extended or adjusted under 35 U.S.C. 154(b) by 216 days.

(21) Appl. No.: 13/183,333

(22) Filed: Jul. 14, 2011

(65) Prior Publication Data

US 2013/0015841 A1    Jan. 17, 2013

(51) Int. Cl.
*G01R 1/20* (2006.01)
*A61B 5/0408* (2006.01)

(52) U.S. Cl.
CPC ....... *A61B 5/04085* (2013.01); *A61B 2562/227* (2013.01)

(58) Field of Classification Search
CPC ...... G01R 1/22; G01R 1/203; G01R 19/0092; G01R 15/207; G01R 15/181; G01R 31/2834; G01R 31/2884; G01R 31/31907; G01R 31/31924; G01R 22/065; G01N 27/02; G01N 27/06; G01N 27/07; G01N 27/023
USPC ........... 324/126, 73.1, 76, 157, 439; 600/388, 600/389, 392, 393
See application file for complete search history.

(56) References Cited

U.S. PATENT DOCUMENTS

| | | | | |
|---|---|---|---|---|
| 3,409,007 A | * | 11/1968 | Fuller | 600/382 |
| 4,608,987 A | * | 9/1986 | Mills | 600/389 |
| 4,861,183 A | * | 8/1989 | Loos | 403/354 |
| 5,192,214 A | * | 3/1993 | Samarov et al. | 439/67 |
| 5,733,151 A | * | 3/1998 | Edsall et al. | 439/729 |
| 6,219,568 B1 | * | 4/2001 | Kelly et al. | 600/386 |
| 6,561,841 B2 | * | 5/2003 | Norwood et al. | 439/489 |
| 6,795,722 B2 | * | 9/2004 | Sheraton et al. | 600/391 |
| 7,439,449 B1 | * | 10/2008 | Kumar et al. | 174/254 |
| 7,446,261 B2 | * | 11/2008 | Kumar et al. | 174/254 |
| 7,967,644 B2 | * | 6/2011 | Pepe et al. | 439/676 |
| 2004/0015194 A1 | * | 1/2004 | Ransbury et al. | 607/10 |
| 2007/0126971 A1 | * | 6/2007 | Lo | 349/149 |

FOREIGN PATENT DOCUMENTS

WO    WO2010/132923 A1 *  11/2010

* cited by examiner

*Primary Examiner* — Huy Q Phan
*Assistant Examiner* — Giovanni Astacio-Oquendo
(74) *Attorney, Agent, or Firm* — Foster Pepper PLLC; Richard A. Koske; Richard C. Vershave (57) ABSTRACT

A system for connecting remote equipment to a sensor device having a connector coupled to at least two terminals located on different portions of the sensor device. The portions of the sensor device may be an anterior portion and a posterior portion with each having at least one terminal. In turn, the terminals are nested on top of one another and at least one terminal is electrically accessible through a window region of the other portion. Further, the terminals are alignable with each other and with a connector by alignment indicators, which may provide a visual alignment indication for the terminals as well as a mechanical alignment of the connector with the sensor device.

4 Claims, 10 Drawing Sheets

CONNECTION SYSTEM FOR SENSOR DEVICE

FIELD OF THE INVENTION

This invention relates generally to sensor devices and, more specifically, to a system and apparatus for connecting the sensor device to remote equipment.

BACKGROUND OF THE INVENTION

Electrocardiogram devices employing twelve or more leads are known. For systems using more than 12 leads, such as 80 lead systems, the electrodes may be deployed as part of a sensor device, such as an electrode vest, which is adhered to a patient. By way of example, one type of electrode vest is described in U.S. Pat. No. 6,055,448. These vests are typically made of a flexible material that includes a dielectric substrate upon which are conductive traces that couple sensor electrodes to multiple terminal areas on the device. Remote equipment, such as an electrocardiogram (ECG) base unit, is generally attached to the sensor device with multiple connectors, typically one for each separate terminal area of the electrode vest.

Figure 1:
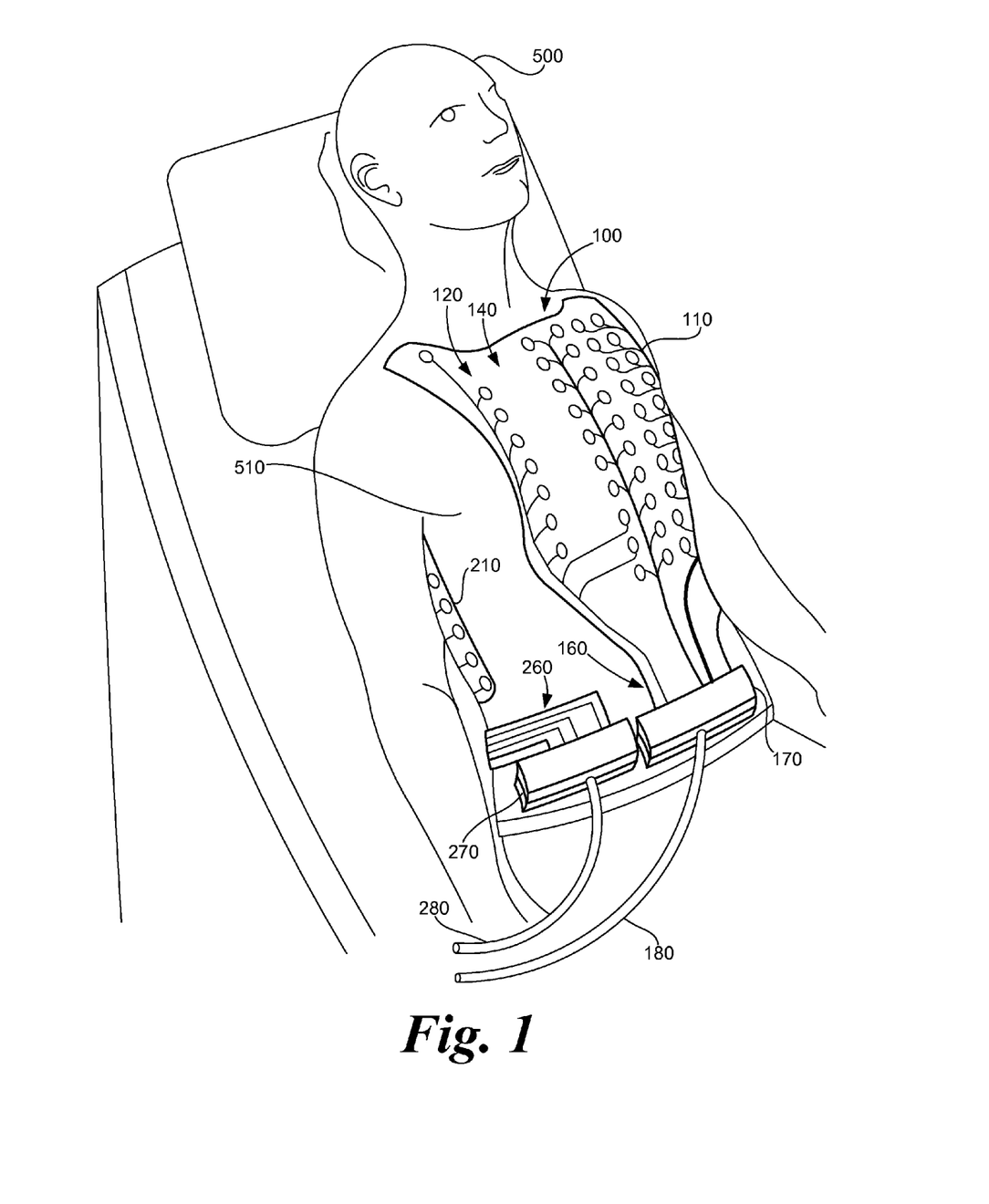
FIG. 1 is a perspective view of a conventional sensor device positioned on a human patient.

FIG. 1 illustrates a sensor device 100 in the form a vest placed on a human patient 500 for either monitoring bioelectric signals from the patent 500 or delivering stimulus signals to the patent 500. The vest 100 includes an anterior portion 110 for placing onto the front of the patient's torso and a posterior portion 210 for placing on the back of the patient's torso. Anterior portion 110 includes a plurality of electrodes 120 connected by a network of conductive traces 140 to a terminal portion 160. Posterior portion 210 (only partially shown, but understood to be placed on the back and sides of the human patient) also includes a plurality of electrodes connected by a network of conductive traces to a terminal portion 260. As shown in FIG. 1, both anterior terminal portion 160 and posterior terminal portion 260 are positioned generally at the front 510 of the patient.

An anterior connector 170 and a posterior connector 270 are connected to the respective anterior and posterior terminal portions 160, 260. The connectors are further in electronic and/or signal communication with remote equipment, such as the connectors in electronic communication with an electrocardiogram (ECG) base unit (not shown) by electrical or fiber-optic cables 180, 280. The user must take care to correctly configure the connectors 170, 270 and terminal portions 160, 260 to avoid errors, either in monitoring the patient's bioelectric signals or in supplying stimulating signals to the patient.

SUMMARY OF THE INVENTION

In accordance with an embodiment of the present invention, an electrode system includes a sensor device, a first conductive terminal located on the sensor device, a second conductive terminal located proximate to and registered with respect to the first conductive terminal on the sensor device, and a connector electrically coupled to both the first and second conductive terminals.

In accordance with another example of the invention, a sensor vest engageable with a connector includes a first electrode mounting portion having a first conductive terminal and a first window located proximate the first conductive terminal, a second electrode mounting portion having a second conductive terminal and a second window located proximate the second conductive terminal, wherein the first window is configured to provide electrical access to the second conductive terminal when the first and second conductive terminals are placed proximate each other, and wherein the second window is configured to provide electrical access to the first conductive terminal when the first and second conductive terminals are placed proximate each other.

In accordance with yet another example of the invention, a sensor vest engageable with a connector includes a first electrode mounting portion having a first conductive terminal and a first alignment indicator, a second electrode mounting portion having a second conductive terminal and a second alignment indicator, and wherein registering the first and second alignment indicators in an overlapping manner provides a visual indication that the first and second conductive terminals are electrically accessible.

These and other examples of the invention will be described in further detail below.

BRIEF DESCRIPTION OF THE DRAWINGS

Preferred and alternative examples of the present invention are described in detail below with reference to the following drawings.

DETAILED DESCRIPTION OF THE PREFERRED EMBODIMENT

As previously discussed, conventional electrode vests may be used in situations when more than twelve electrodes, possibly as many as 80 or more, are to be applied to a human patient. These electrode vests usually have multiple terminal areas that require separate connectors for communicating with remote equipment, such as electrocardiogram (ECG) base units. The use of multiple connectors increases the complexity of coupling the sensor device to the remote equipment and may also increase the cost of the overall system. Accordingly, there is a need for a less complex and less costly system and apparatus that allows a sensor device with multiple traces and multiple terminals to be coupled to the remote equipment.

Figure 2:
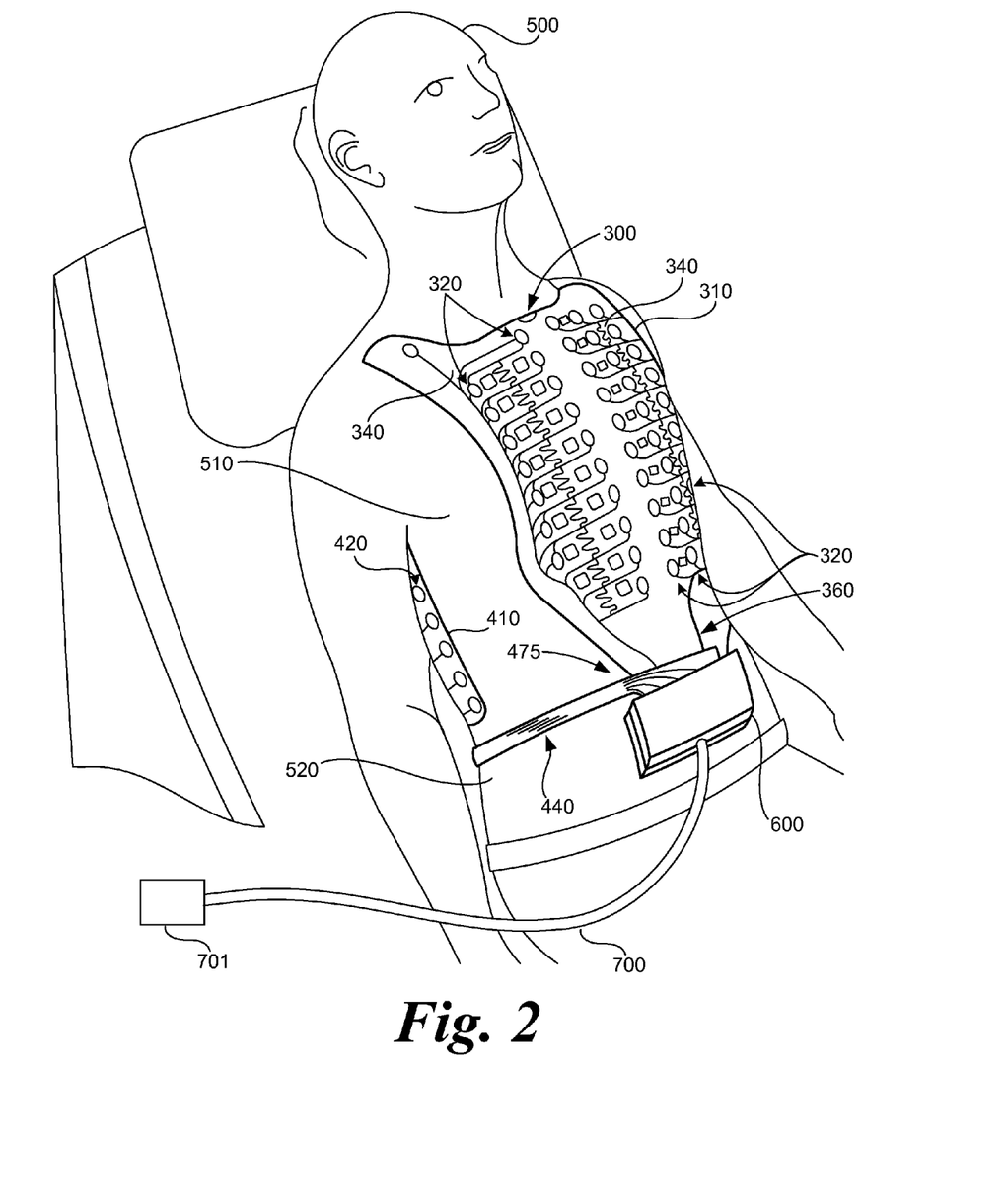
FIG. 2 is a perspective view of a sensor device according to an embodiment of the present invention positioned on a human patient.

FIG. 2 illustrates a sensor device 300 in the form an electrode vest according to an embodiment of the present invention. As illustrated in FIG. 2, vest 300 is placed onto a human patient 500 for either monitoring bioelectric signals from the patient 500 or delivering stimulus signals to the patient 500. The vest 300 includes a first electrode mounting portion, such as anterior portion 310 (FIG. 3) for placing onto the front of the patient's torso and a second electrode mounting portion, such as posterior portion 410 for placing onto the back of the patient's torso. Anterior portion 310 includes a plurality of electrodes 320 connected by a network of conductive traces 340 to a terminal portion 360. Posterior portion 410 (only partially shown in FIG. 2, but understood to be placed on the back and sides of the human patient) also includes a plurality of electrodes 420 connected by a network of conductive traces 440 to a terminal portion 475. As shown in FIG. 2, and as described more fully below, both anterior and posterior terminal portions 360, 475 are coupled by a single connector 600 and multi-conductor cable 700 to remote equipment 701, such as, but not limited to, an electrocardiogram (ECG) base unit.

Figure 3:
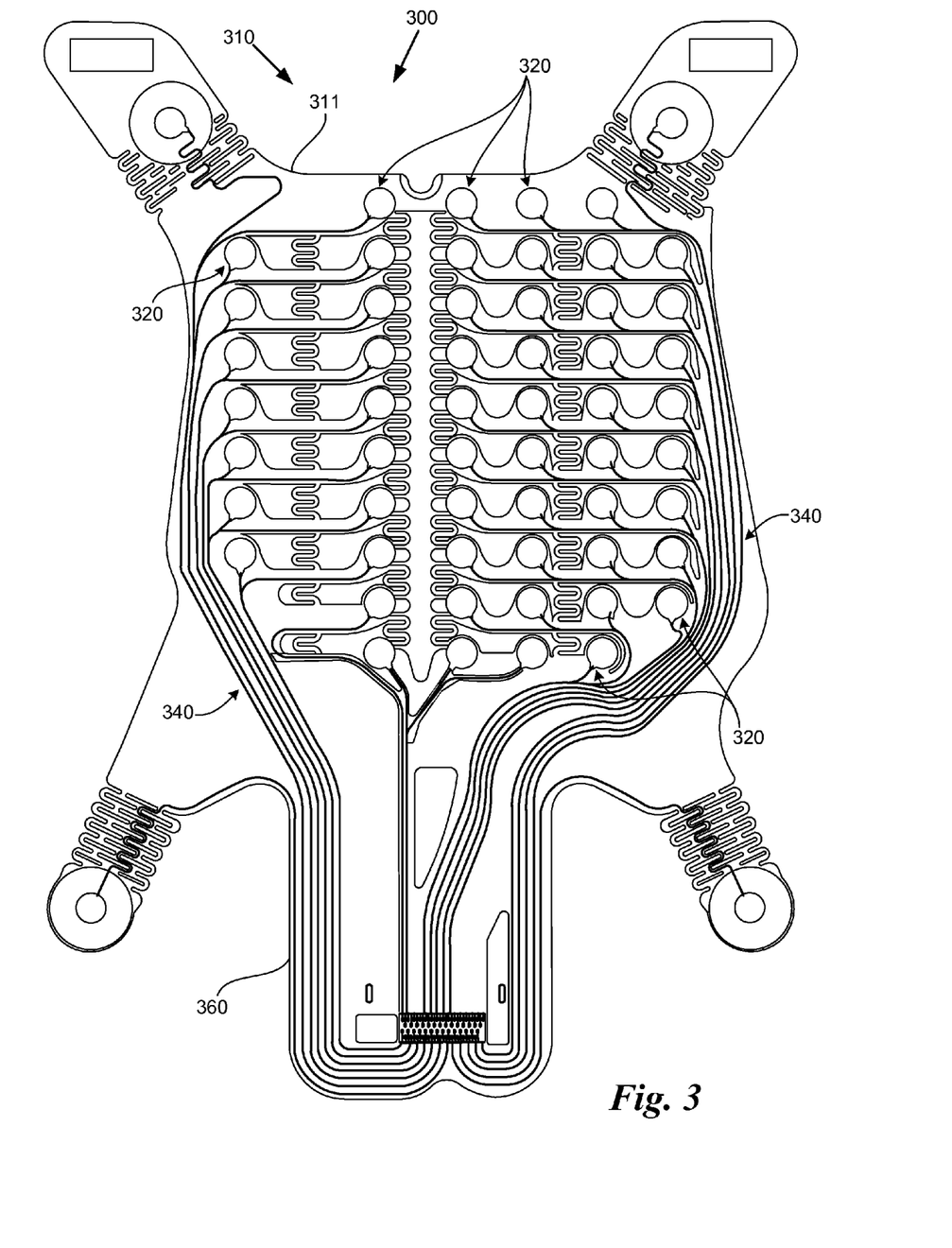
FIG. 3 is a plan view of an anterior portion of the sensor device of FIG. 2.
Figure 4:
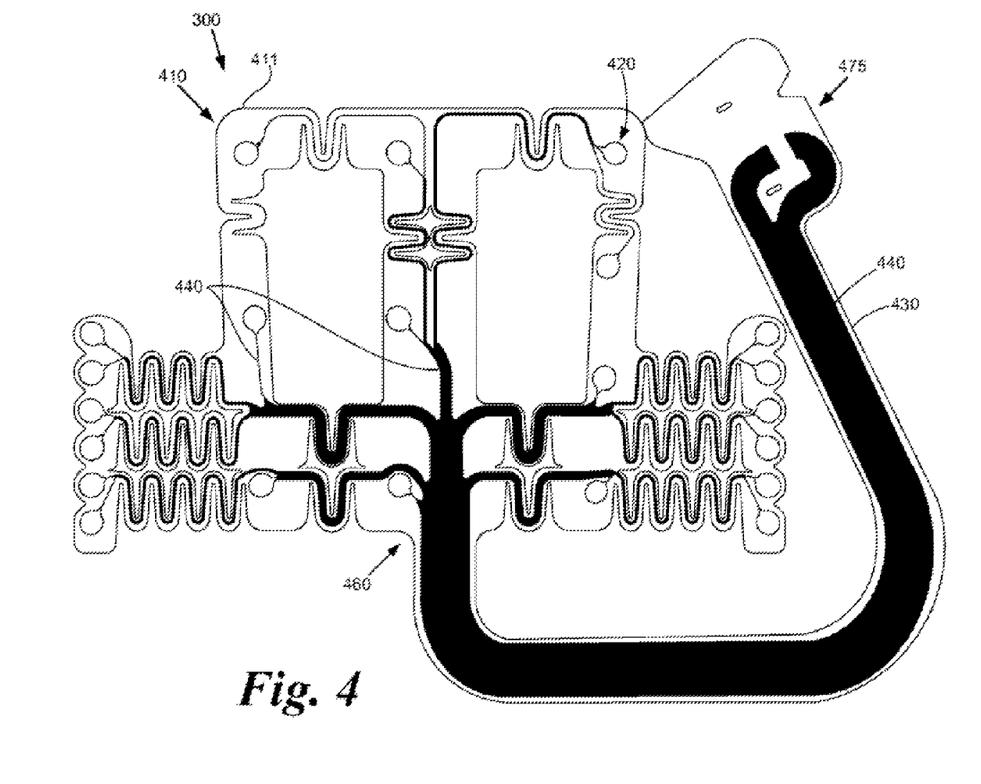
FIG. 4 is a plan view of a posterior portion of the sensor device of FIG. 2.

As shown in FIG. 3, the anterior terminal portion 360 is located near the bottom edge of the anterior portion 310 of vest 300. Similarly, FIG. 4 shows the posterior terminal portion 475 at the end of a tail 430 extending from the bottom edge 460 of the posterior portion 410. The tail 430 is wrapped around the patient's torso so that posterior terminal portion 475 is positioned at the front of the patient's body in the vicinity of the anterior terminal portion 360 (see also FIG. 2). For purposes of clarity, the anterior and posterior portions 310, 410 in FIGS. 3 and 4 are illustrated from the side facing away from the patient when the vest 300 is placed onto the patient and it is understood that the electrodes 320, 420 and traces 340, 440 are located on the surface of portions 310, 410 facing the patient. It is further understood that when the vest 300 is placed onto the patient, the electrodes 320, 420 will be in contact with the patient's body. Conductive traces 340, 440 are insulated through conventional methods and materials so as not to contact the patient's body.

Figure 5:
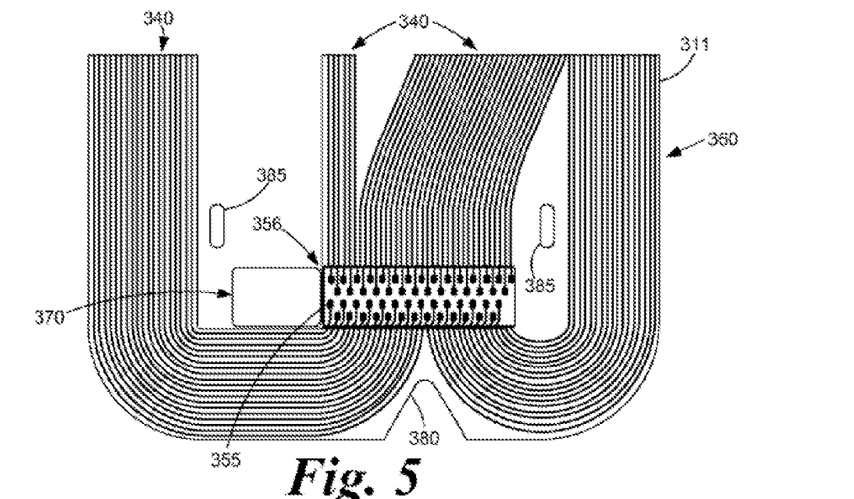
FIG. 5 is a plan view of an anterior terminal portion of the sensor device of FIG. 3.

FIG. 5 illustrates in greater detail the anterior terminal portion 360. An alignment indicator, such as notch 380, is located along a bottom edge of terminal portion 360 and a pair of spaced-apart slots 385 is positioned within the terminal portion 360. A network of insulated conductive traces 340 are connected at one end to sensors or electrodes 320 (FIG. 3) and are terminated at their opposite end at contacts 355 located at contact pad 356 on terminal portion 360. As discussed previously, the traces 340 are insulated with a nonconductive material. However, contacts 355 are not insulated so they may be connected to remote equipment, such as an ECG base unit. Adjacent the contact pad 356 is an open area, or window, 370 in the substrate 311.

Figure 6:
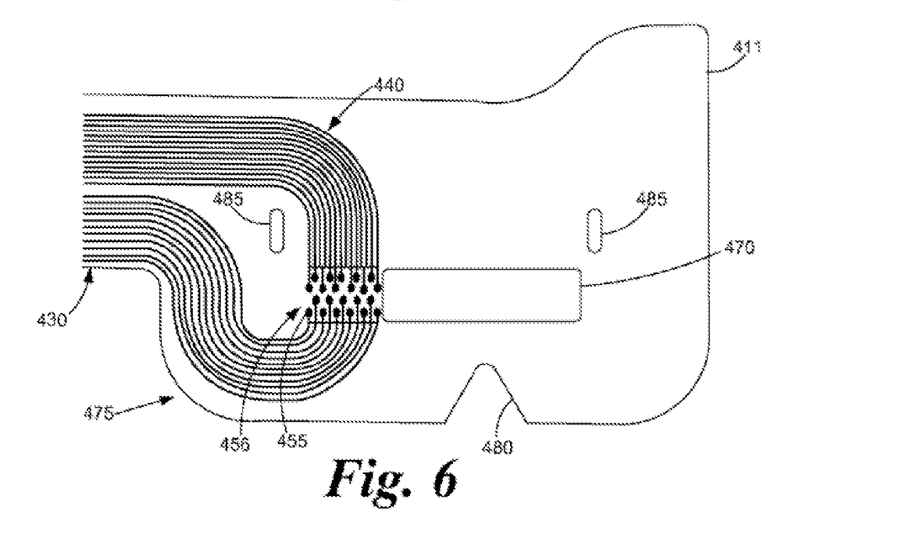
FIG. 6 is a plan view of a posterior terminal portion of the sensor device of FIG. 4.

Turning to FIG. 6 the posterior terminal portion 475 is illustrated in greater detail. An alignment indicator, such as notch 480, is located along a bottom edge of terminal portion 475 and a pair of spaced apart slots 485 is positioned within the terminal portion 475. A network of insulated conductive traces 440 are connected at one end to sensors or electrodes 420 (FIG. 4) and are terminated at their opposite ends at contacts 455 in contact pad 456. Contacts 455 are not insulated. Adjacent the contact pad 456 is an open area, or window, 470 in the substrate 411.

Figure 7:
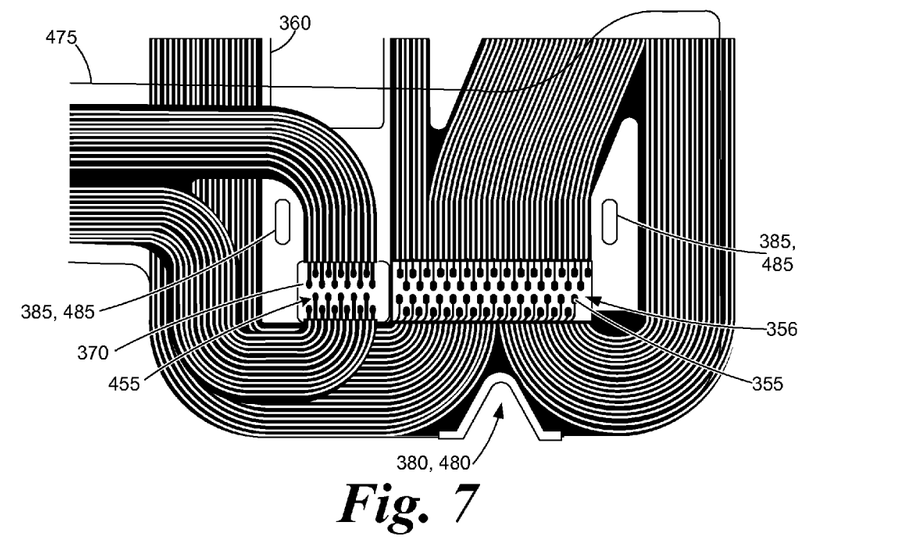
FIG. 7 is a plan view of the posterior terminal portion nested on top of the anterior terminal portion.
Figure 8:
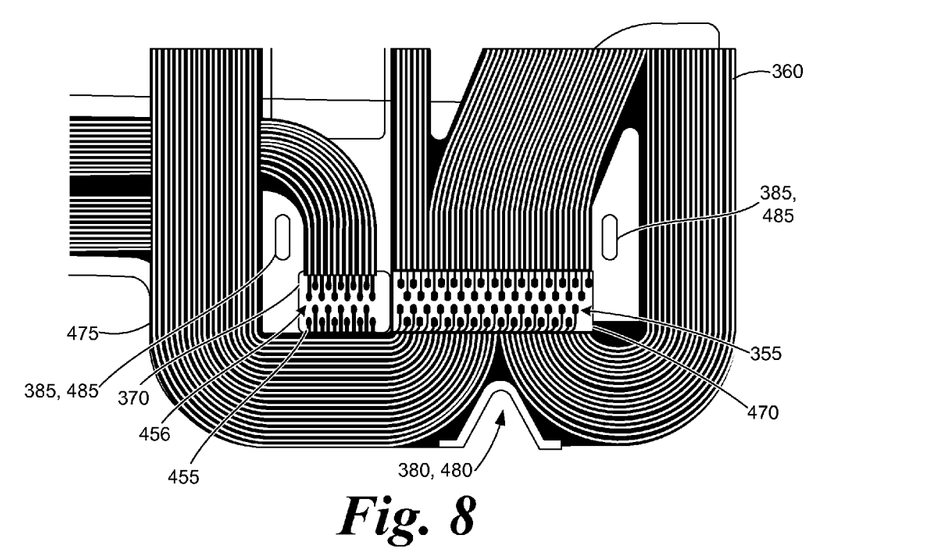
FIG. 8 is a plan view of the anterior terminal portion nested on top of the posterior terminal portion.
Figure 10:
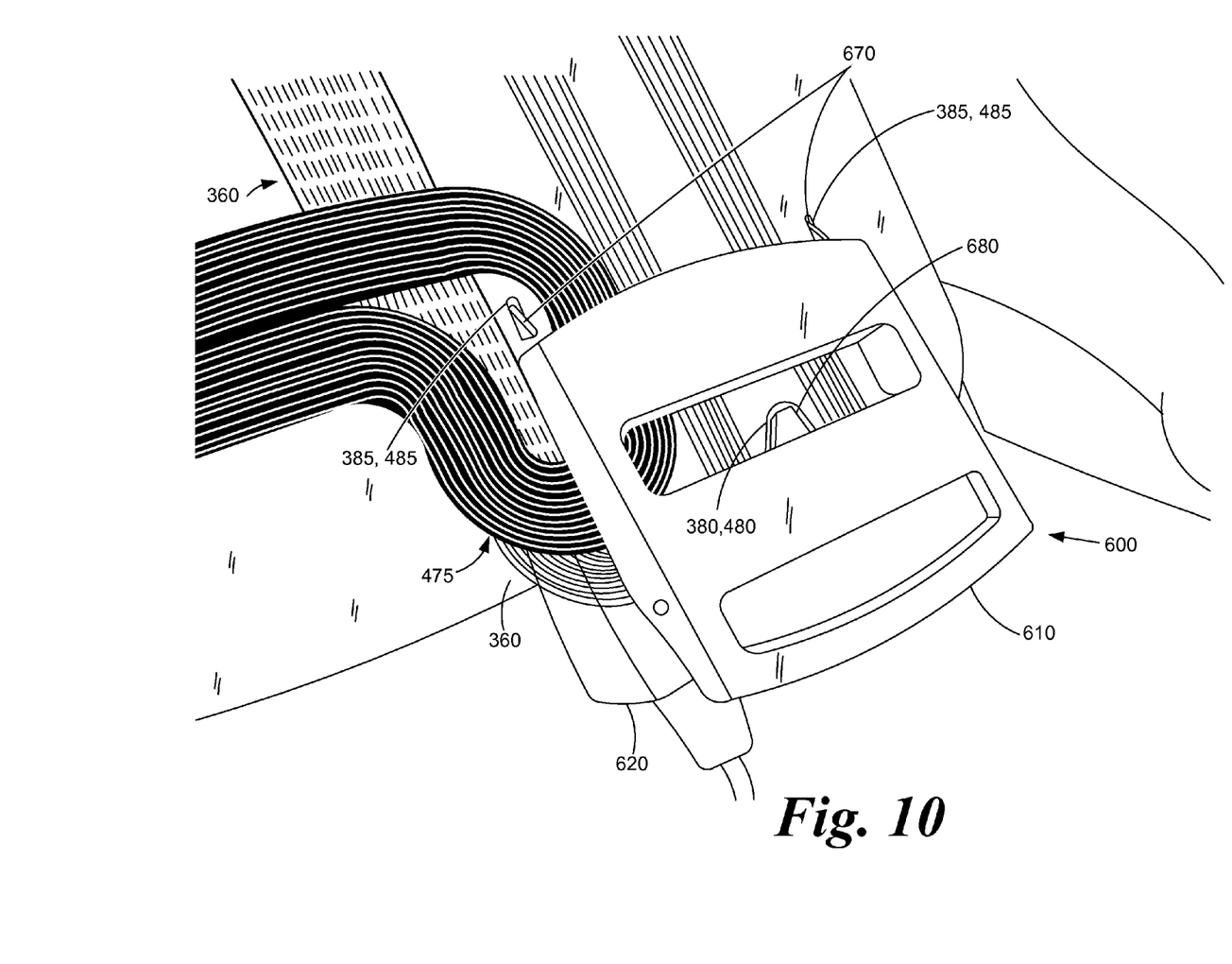
FIG. 10 is a perspective view of the nested terminal portions of FIG. 7 positioned in the connector; and, FIG. 11 is a perspective view of the nested terminal portions of FIG. 8 positioned in the connector.
Figure 11:
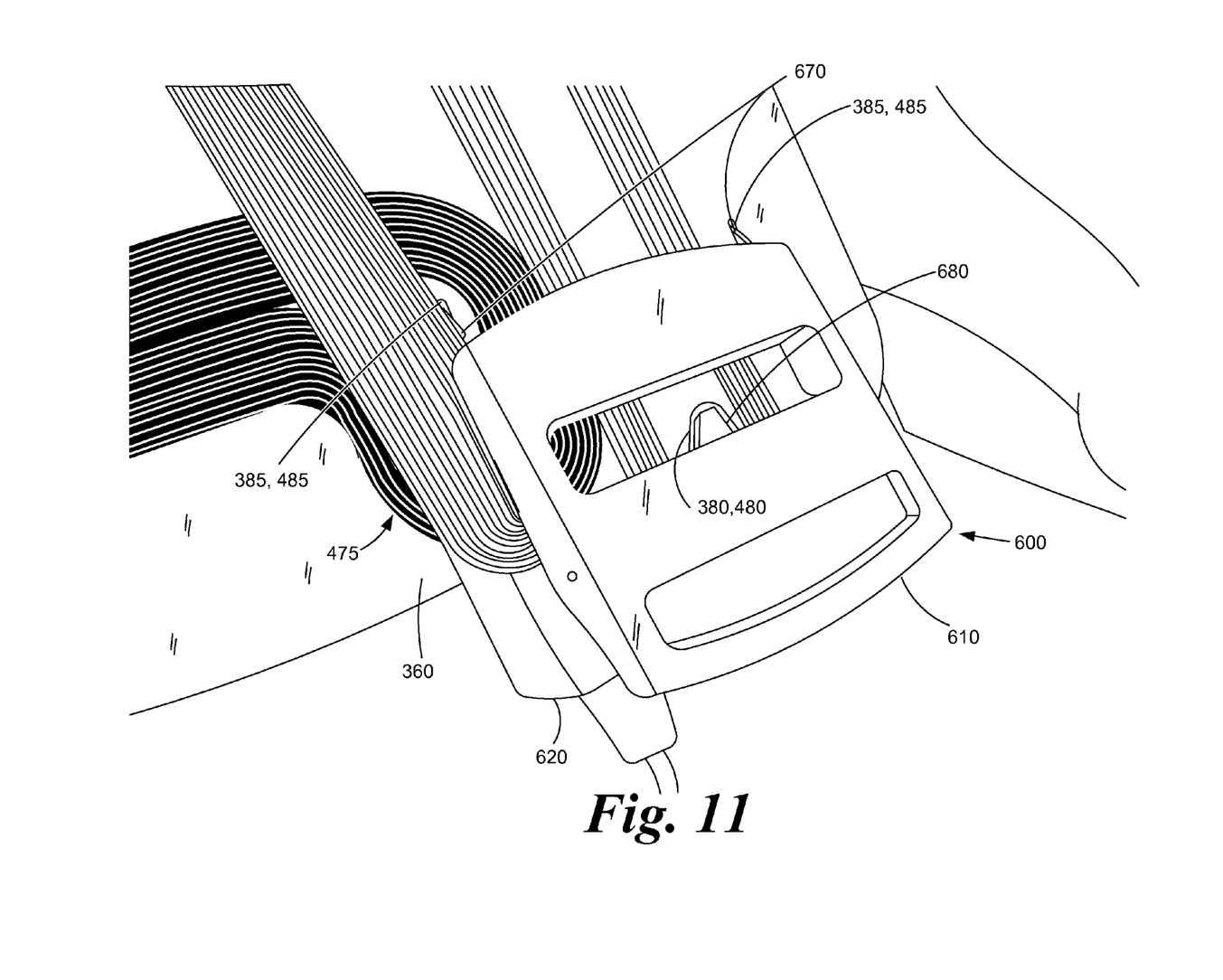

As will be better understood with reference to FIGS. 7 and 8, the anterior and posterior terminal portions 360, 475 may be nested, or placed on top of one another, such that notches 380, 480 and slots 385, 485 are aligned, which in turn permits registration of the terminal portions 360, 475 with respect to each other. Further, as illustrated in FIG. 7, with posterior terminal portion 475 placed on top of the anterior terminal portion 360, the contacts 455 of the posterior contact pad 456 are exposed through window 370. Likewise, as illustrated in FIG. 8, in which the anterior terminal portion 360 is positioned on top of the posterior terminal portion 475, the contacts 355 of the anterior contact pad 356 are exposed through window 470. As can be appreciated from the foregoing description, nesting the anterior and posterior terminal portions 360, 475 aligns notches 380, 480 and slots 385, 485 and allows the contacts 355, 455 of both terminal portions to be accessed from the same side of the vest 300 by one connector 600 (FIGS. 10, 11).

Figure 9A:
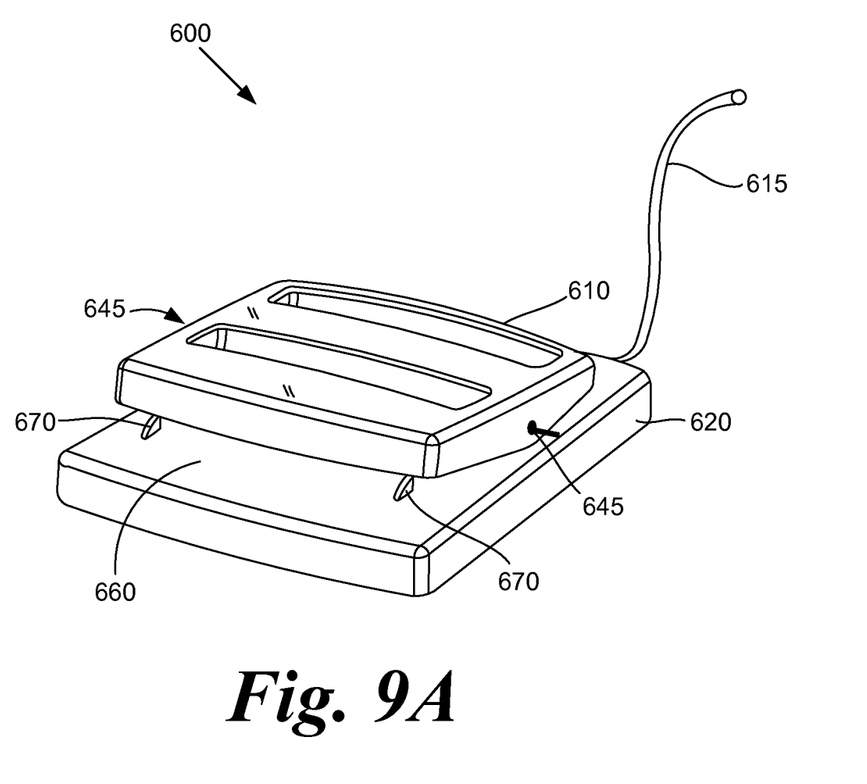
FIG. 9A is a perspective view of the connector of FIG. 2.

FIG. 9A shows a connector 600 suitable for connecting to the nested terminal portions 360, 475 (FIGS. 7, 8). Top 610 is pivotally attached to base 620 by means of rod 640 (FIG. 9B), which passes through pivot support 630 and holes 645 on either side of top 610. Springs 650 are mounted to base 620 and bias a front edge of the top 610 to a closed position in relation to the base 620. The connector 600 is shown in the open position in FIG. 9A, with springs 650 compressed, as would be its state when the top 610 and base 620 are pinched by a user/operator to compress springs 650.

Figure 9B:
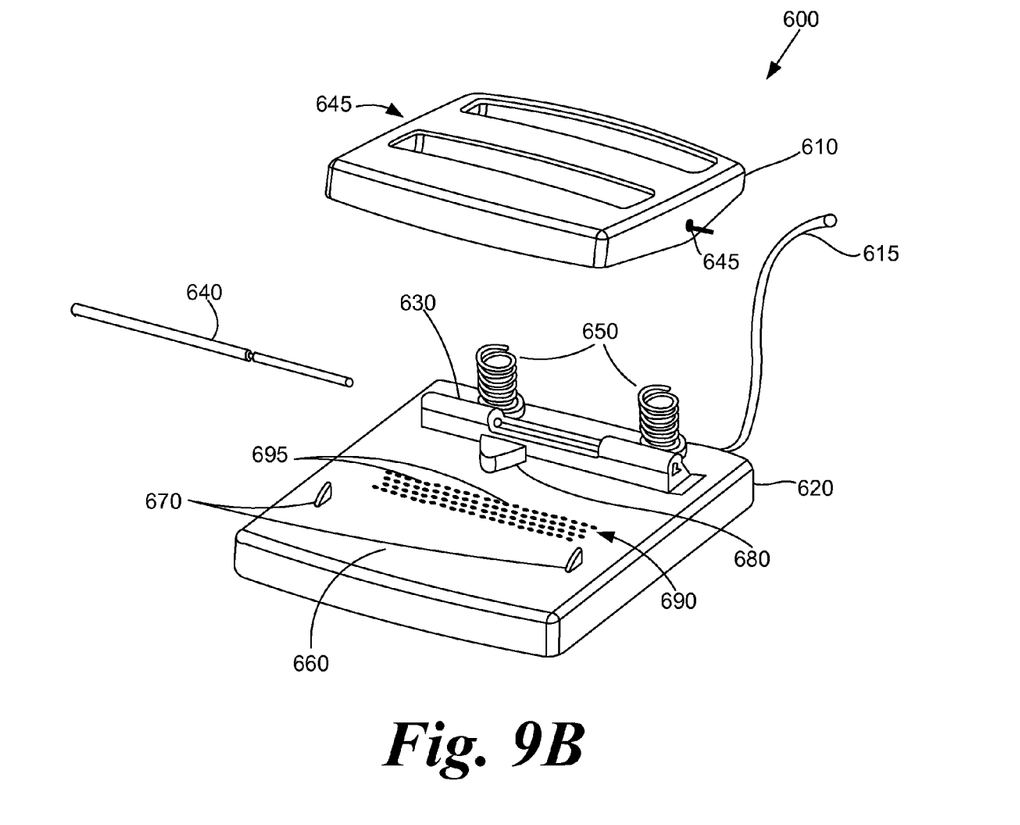
FIG. 9B is an exploded, perspective view of the connector of FIG. 9A.

FIG. 9B shows an exploded view of connector 600 to better illustrate various components of connector 600. As will be better understood from the description below and with reference to FIGS. 10 and 11, alignment element 680 and tabs 670 act to align and secure the nested anterior and posterior terminal portions 360, 475 of device 300 when they are placed in the connector 600. When so placed in the connector 600, and with connector 600 closed, contacts 355, 455 are electrically coupled through conductive pins 695 on connector 600 to the ECG base unit or other remote equipment.

According to one embodiment of the present invention, the alignment element 680 shown in FIG. 9B is a raised, wedge-shaped shoulder located on the base generally adjacent the pivot support 630 and on a surface of the base facing the top 610. The alignment element 680 in other embodiments may have a different shape, such as square or an irregular shape. Also, the alignment element 680 may reside in a different position on the connector 600 or may be implemented as more than one aligning member on the connector 600. The two spaced-apart, retaining tabs 670 are located away from the pivot support 630 on the surface of the base 620 facing the top 610. In other embodiments of the present invention, the retaining tabs 670 may be positioned differently on the connector 600, in fewer or greater number and may have a different shape, such as a cylindrical pin, for example. Contact pad 690 is located on the surface of the base 620 facing the top 610 and includes the array of electrically conductive pins 695 that are coupled to one end of cable 615. Cable 615 is connected at the other end (not shown) to remote equipment, such as an ECG base unit (also not shown).

Turning to FIG. 10, posterior terminal portion 475 is positioned on top of the anterior terminal portion 360 and positioned in closed connector 600. The nested terminal portions 475, 360 are positioned in connector 600 such that contacts 355, 455 are in electrical contact with respective pins 695 located on the base 620 of the connector 600.

FIG. 11 illustrates the opposite situation in which the anterior terminal portion 360 is positioned on top of the posterior terminal portion 475 and contacts 355, 455 are in electrical contact with respective pins 695 on connector 600. In both orientations illustrated in FIGS. 10 and 11, the alignment element 680 is seated with the notches 380, 480 to align the terminal portions 360, 475 with the connector 600 and the retaining tabs 670 are engaged with the slots 385, 485 to hold the terminal portions 360, 475 in the connector 600 when the connector 600 is in the closed position.

As is appreciated from the foregoing discussion, the present invention provides a system and apparatus for connecting multiple terminal portions on an electrode vest with a single connector. Further, the different terminal portions of the vest may be nested in different orientations and still fit into, and make electrical contact with, contacts in the connector. As can be appreciated, the present invention provides and simple, versatile and inexpensive system and apparatus for connecting to multiple terminal areas of an electrode vest.

While the preferred embodiment of the invention has been illustrated and described, as noted above, many changes can be made without departing from the spirit and scope of the invention. For example, the shape, quantity and position of the aligning shoulder and retention tabs may be different than as described and illustrated. Likewise the orientation and geometry of the contact pads and windows may differ. Accordingly, the scope of the invention is not limited by the disclosure of the preferred embodiment. Instead, the invention should be determined entirely by reference to the claims that follow.

The embodiments of the invention in which an exclusive property or privilege is claimed are defined, as follows:

1. A sensor device for a human patient, the sensor device comprising:
   a connector;
   a first electrode mounting portion having a first substrate surface with a first conductive terminal applied onto the first substrate surface, the first substrate surface having a first window and a first alignment element formed in the first substrate surface; and
   a second electrode mounting portion having a second substrate surface with a second conductive terminal applied onto the second substrate surface, the second substrate having a second window and a second alignment element formed in the second substrate surface,
   wherein alignment of the first and second alignment elements includes overlapping, in a planar manner, the first and second substrate surfaces to register the first and second windows, and
   wherein registration of the first and second windows permits electrical communication between the first and second conductive terminals and the connector when any of the first and second conductive terminals is positioned on top of one another.

2. The sensor device of claim 1, wherein the first conductive terminal is positioned on top of the second conductive terminal when the first and second alignment elements are in overlapping registration.

3. The sensor device of claim 1, wherein the second conductive terminal is positioned on top of the first conductive terminal when the first and second alignment elements are in overlapping registration.

4. A sensor vest comprising:
   a connector having a housing with retaining tabs and contact pins;
   a first vest mounting portion having a first conductive terminal with a plurality of first electrical contacts, the first conductive terminal configured with a first notch and a first slot, the first notch and the first slot residing in a first substrate plane; and
   a second vest mounting portion having a second conductive terminal with a plurality of second electrical contacts, the second conductive terminal configured with a second notch and a second slot, the second notch and the second slot residing in a second substrate plane,
   wherein alignment of the first and second notches in a planar, overlapping manner permits the first electrical contacts and the second electrical contacts to be electrically engaged with the when any of the first and second conductive terminals is positioned on top of one another.

* * * * *